(12) United States Patent
Hori et al.

(10) Patent No.: US 12,233,156 B2
(45) Date of Patent: Feb. 25, 2025

(54) MICRONEEDLE DEVICE AND METHOD FOR PRODUCING THE SAME

(71) Applicant: HISAMITSU PHARMACEUTICAL CO., INC., Tosu (JP)

(72) Inventors: Ryota Hori, Tsukuba (JP); Shinpei Nishimura, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 1012 days.

(21) Appl. No.: 17/253,311

(22) PCT Filed: Jun. 20, 2019

(86) PCT No.: PCT/JP2019/024586
§ 371 (c)(1),
(2) Date: Dec. 17, 2020

(87) PCT Pub. No.: WO2020/004234
PCT Pub. Date: Jan. 2, 2020

(65) Prior Publication Data
US 2021/0267882 A1 Sep. 2, 2021

(30) Foreign Application Priority Data
Jun. 26, 2018 (JP) .................................. 2018-120639

(51) Int. Cl.
*A61M 37/00* (2006.01)
*A61K 9/00* (2006.01)
(Continued)

(52) U.S. Cl.
CPC ........ *A61K 9/0021* (2013.01); *A61K 31/4174* (2013.01); *A61K 47/36* (2013.01);
(Continued)

(58) Field of Classification Search
CPC ...... A61M 37/0015; A61M 2037/0023; A61M 2037/0046; A61M 2037/0053; A61M 2037/0061; A61K 9/0021
See application file for complete search history.

(56) References Cited

U.S. PATENT DOCUMENTS 5,124,157 A 6/1992 Colley et al.
8,242,158 B1 8/2012 Roychowdhury et al.
(Continued)

FOREIGN PATENT DOCUMENTS

CN 1863571 A 11/2006
CN 102112151 A 6/2011
(Continued)

OTHER PUBLICATIONS

English translation of WO2016/039418 A1. (Year: 2016).*
(Continued)

*Primary Examiner* — Kami A Bosworth
(74) *Attorney, Agent, or Firm* — Nath, Goldberg & Meyer; Joshua B. Goldberg

(57) ABSTRACT

The present invention aims to manufacture a microneedle device capable of carrying and administering a larger amount of biologically active substance per one microneedle. One aspect of the present invention is a method of manufacturing a microneedle device comprising coating microneedles with a coating liquid, wherein the coating liquid comprises a biologically active substance and a sulfated polysaccharide. The microneedle device manufactured by such a method comprises a substrate, microneedles disposed on the substrate, and a coating formed on the microneedles, wherein the coating comprises a biologically active substance and a sulfated polysaccharide.

8 Claims, 8 Drawing Sheets

(51) Int. Cl.
*A61K 31/4174* (2006.01)
*A61K 47/36* (2006.01)

(52) U.S. Cl.
CPC . *A61M 37/0015* (2013.01); *A61M 2037/0023* (2013.01); *A61M 2037/0053* (2013.01); *A61M 2205/0238* (2013.01)

(56) References Cited

U.S. PATENT DOCUMENTS

| | | | |
|---|---|---|---|
| 2008/0233179 | A1 | 9/2008 | Grenier et al. |
| 2011/0288485 | A1* | 11/2011 | Tokumoto ............ A61K 9/0021 604/173 |
| 2012/0095104 | A1 | 4/2012 | Zachar et al. |
| 2014/0066842 | A1 | 3/2014 | Zhang et al. |
| 2015/0098980 | A1 | 4/2015 | Pongpeerapat et al. |
| 2016/0001053 | A1* | 1/2016 | Quan ................ A61M 37/0015 427/2.31 |
| 2016/0271380 | A1 | 9/2016 | Poon et al. |
| 2017/0080196 | A1 | 3/2017 | Lee et al. |
| 2017/0266427 | A1 | 9/2017 | Nishimura et al. |
| 2019/0350840 | A1 | 11/2019 | Hori et al. |
| 2021/0267882 | A1 | 9/2021 | Hori et al. |

FOREIGN PATENT DOCUMENTS

| | | |
|---|---|---|
| CN | 102300566 A | 12/2011 |
| CN | 102395354 A | 3/2012 |
| CN | 102770176 A | 11/2012 |
| CN | 103402496 A | 11/2013 |
| CN | 105073180 A | 11/2015 |
| CN | 103402496 B | 1/2016 |
| CN | 105764494 A | 7/2016 |
| CN | 107106658 A | 8/2017 |
| CN | 110114069 A | 8/2019 |
| CN | 110201297 A | 9/2019 |
| EP | 2540337 A1 | 1/2013 |
| EP | 3560495 A1 | 10/2019 |
| JP | 63-79820 A | 4/1988 |
| JP | 6-503916 A | 6/1993 |
| JP | 2001-506904 A | 5/2001 |
| JP | 2010-029634 A | 2/2010 |
| JP | 2012-90767 A | 5/2012 |
| JP | 2014-507473 A | 3/2014 |
| JP | 2014-508746 A | 4/2014 |
| JP | 2014-79557 A | 5/2014 |
| JP | 2016-83085 A | 5/2016 |
| JP | 2016-532642 A | 10/2016 |
| JP | 2016-196510 A | 11/2016 |
| JP | 2017-105784 A | 6/2017 |
| KR | 20120138235 A | 12/2012 |
| KR | 20140013022 A | 2/2014 |
| KR | 20150118136 A | 10/2015 |
| KR | 20150126413 A | 11/2015 |
| KR | 101745682 B1 | 6/2017 |
| TW | 201309331 A | 3/2013 |
| TW | I519781 B | 2/2016 |
| WO | 98/28037 A1 | 7/1998 |
| WO | 2010/063030 A2 | 6/2010 |
| WO | 2012115207 A1 | 8/2012 |
| WO | 2012122162 A1 | 9/2012 |
| WO | 2013103378 A1 | 7/2013 |
| WO | 2016/039418 A1 | 3/2016 |
| WO | 2017159767 A1 | 9/2017 |
| WO | 2017180788 A1 | 10/2017 |
| WO | 2018123982 A1 | 7/2018 |
| WO | 2020004234 A1 | 1/2020 |

OTHER PUBLICATIONS

Zhu, et al. "Research Progress in Transdermal Deliver Technology of Micro Needle"; 2016.
International Preliminary Report on Patentability (IPRP) dated Jul. 2, 2019 issued in corresponding International Application No. PCTJP2017/046456.
Kivisto, K . T. et al."Pharmacokinetics and pharmacodynamics of transdermal dexmedetomidine", European Journal of Clinical Pharmacology; Springer Verlag, DE; vol. 46, No. 4; Jan. 1, 1994; p. 345-349, XP008124147.
Extended European Search Report dated Jul. 3, 2020 corresponding to application No. 17888272.6-1109.
International Search Report dated Feb. 6, 2018 issued in corresponding International Application No. PCT/JP2017/046456.
Sodium Metabisulfite, retrieved from the Internet at https://en.wikipedia.org/wiki/Sodium_metabisulfite on Mar. 24, 2020. (Year: 2020).
International Search Report dated Sep. 17, 2019 corresponding to application No. PCT/JP2019/024586.
Extended European Search Report dated Feb. 24, 2022 corresponding to application No. 19824984.9.
International Preliminary Report on Patentability dated Jan. 7, 2021 corresponding to application No. PCT/JP2019/024586.
Smith, G. et al., "Effects of ascorbic acid and disodium edetate on the stability of isoprenaline hydrochloride injection", Journal of Clinical and Hospital Pharmacy, 1984, vol. 9, p. 209-p. 215.
Extended European Search Report dated Jan. 9, 2024 corresponding to application No. 20906105.0-1109.
Feng Nianping, "Chinese Medicine Percutaneous Administration And Functional Cosmetics", China Pharmaceutical Science and Technology Press, May 31, 2019, p. 123, the 4th line-p. 125.

* cited by examiner

MICRONEEDLE DEVICE AND METHOD FOR PRODUCING THE SAME

This is a National Phase Application filed under 35 U.S.C. 371 as a national stage of PCT/JP2019/024586, filed Jun. 20, 2019, an application claiming the benefit of Japanese Application No. 2018-120639, filed Jun. 26, 2018, the content of each of which is hereby incorporated by reference in its entirety.

TECHNICAL FIELD

The present invention relates to a microneedle device and a method for manufacturing the same.

BACKGROUND ART

As a form of administering a drug, transdermal administration using a microneedle device is known. The microneedle device allows a drug to be transdermally administered by piercing the stratum corneum, which is the outermost layer of the skin, with microneedles to form micropores through which the drug passes. The microneedle device comprises, for example, a substrate, microneedles disposed on the substrate, and a coating formed on the microneedles, and the coating comprises a biologically active substance (for example, Patent Literature 1).

CITATION LIST

Patent Literature

[Patent Literature 1] Japanese Unexamined Patent Publication No. 2014-507473

SUMMARY OF INVENTION

Technical Problem

In order to curb skin irritation due to the use of a microneedle device, it is conceivable to reduce the number (a density) of microneedles per unit area. However, when the number of microneedles is reduced, the amount of the biologically active substance that can be administered correspondingly decreases, and thus sufficient medicinal effects may not be exhibited. Accordingly, an object of the present invention is to manufacture a microneedle device capable of carrying and administering a larger amount of biologically active substance per one microneedle.

Solution to Problem

A microneedle device according to an aspect of the present invention comprises a substrate, microneedles disposed on the substrate, and a coating formed on the microneedles, wherein the coating comprises a biologically active substance and a sulfated polysaccharide.

The sulfated polysaccharide may be one or more sulfated polysaccharides selected from the group consisting of chondroitin sulfate, carrageenan, fucoidan, ascophyllan, heparin, heparan sulfate, heparin analogue, keratan sulfate, funoran, porphyran, agaropectin, furcellaran, rhamnan sulfate, glucuronoxylorhamnan sulfate, xyloarabinogalactan sulfate, glucuronoxylorhamnogalactan sulfate, arabinan sulfate, sulfated dextran, sulfated pentosan, sulfated curdlan, and sulfated cellulose, and salts thereof, and is preferably sodium chondroitin sulfate. The biologically active substance may be dexmedetomidine or a pharmaceutically acceptable salt thereof. An amount of the sulfated polysaccharide may be 0.5 parts by mass or more with respect to 100 parts by mass of the coating. A mass ratio of the sulfated polysaccharide to the biologically active substance may be 0.01 to 0.36, preferably 0.011 to 0.222, and more preferably 0.089 to 0.222. The microneedles may be disposed on the substrate at a needle density of 10 needles/cm$^2$ or more and 850 needles/cm$^2$ or less. An amount of the biologically active substance carried per one microneedle may be 390 ng or more.

A method of manufacturing a microneedle device according to an aspect of the present invention comprises coating the microneedles with a coating liquid, wherein the coating liquid comprises a biologically active substance and a sulfated polysaccharide. The microneedle device comprises a substrate, microneedles disposed on the substrate, and a coating formed on the microneedles.

The sulfated polysaccharide may be one or more sulfated polysaccharides selected from the group consisting of chondroitin sulfate, carrageenan, fucoidan, ascophyllan, heparin, heparan sulfate, heparin analogue, keratan sulfate, funoran, porphyran, agaropectin, furcellaran, rhamnan sulfate, glucuronoxylorhamnan sulfate, xyloarabinogalactan sulfate, glucuronoxylorhamnogalactan sulfate, arabinan sulfate, sulfated dextran, sulfated pentosan, sulfated curdlan, and sulfated cellulose, and salts thereof, and is preferably sodium chondroitin sulfate. The biologically active substance may be dexmedetomidine or a pharmaceutically acceptable salt thereof. A concentration of the sulfated polysaccharide in the coating liquid may be 0.1 mass % or more. A mass ratio of the sulfated polysaccharide to the biologically active substance in the coating liquid may be 0.01 to 0.36, preferably 0.011 to 0.222, and more preferably 0.089 to 0.222.

Advantageous Effects of Invention

According to the present invention, it is possible to manufacture a microneedle device capable of carrying and administering a larger amount of biologically active substance per one microneedle.

DESCRIPTION OF EMBODIMENTS

A method of manufacturing a microneedle device according to an aspect of the present invention comprises a step (coating step) of coating microneedles with a coating liquid. After the coating step, a step (a drying step) of drying the coating liquid may be performed. Here, the microneedle device is a device comprising a substrate, microneedles disposed on the substrate, and a coating formed on the microneedles.

Figure 1:
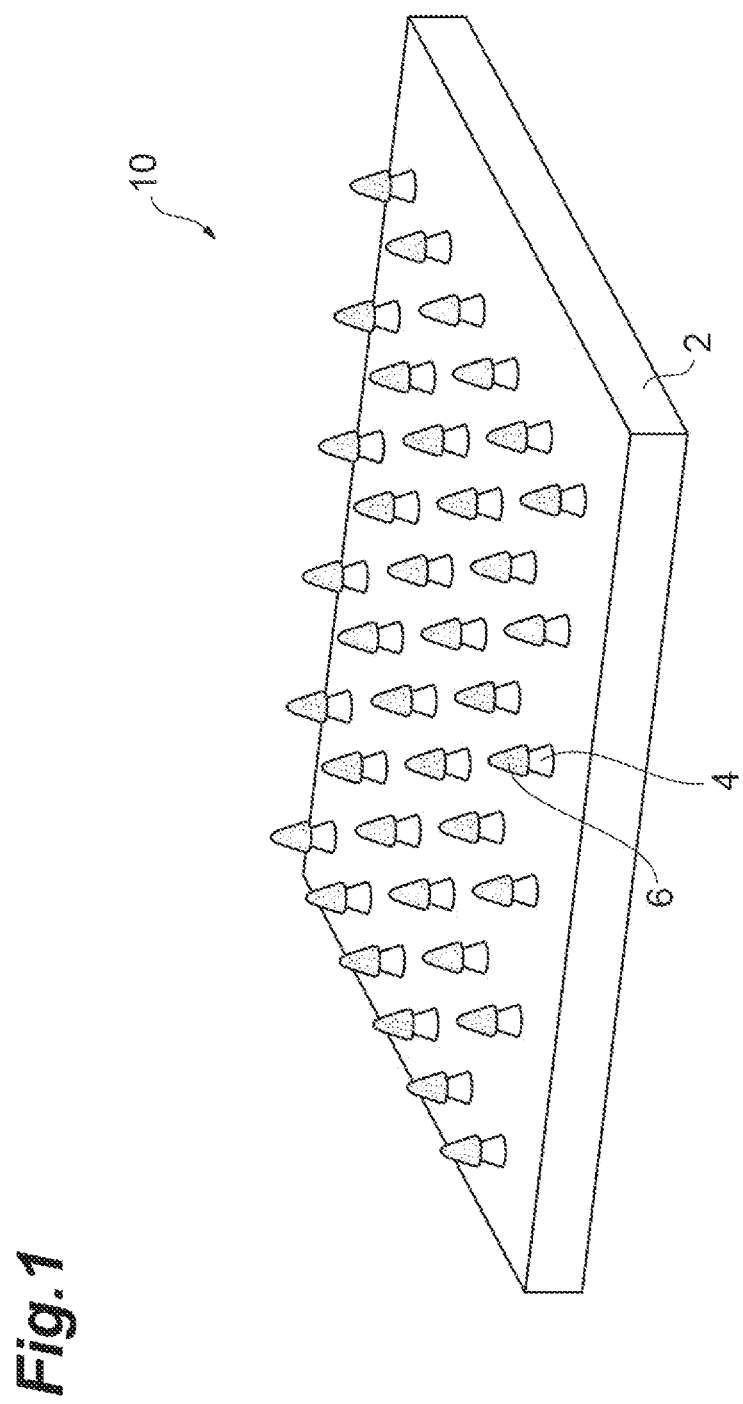
FIG. 1 is a perspective view schematically showing an embodiment of a microneedle device.

One embodiment of the microneedle device of the present invention is shown in FIG. 1. The microneedle device 10 comprises a substrate 2, a plurality of microneedles 4 disposed on a main surface of the substrate 2, and a coating 6 formed on each of the microneedles 4. In the present specification, a configuration in which the plurality of microneedles 4 are disposed on the substrate 2 is referred to as a microneedle array. Details of the coating 6 will be described later.

The substrate 2 is a base for supporting the microneedles 4. A shape and a form of the substrate 2 are not particularly limited and may be, for example, rectangular or circular, and the main surface may be flat or curved. An area of the substrate 2 may be, for example, 0.5 cm$^2$ to 10 cm$^2$, 0.5 cm$^2$ to 5 cm$^2$, 1 cm$^2$ to 5 cm$^2$, 0.5 cm$^2$ to 3 cm$^2$, or 1 cm$^2$ to 3 cm$^2$. A thickness of the substrate 2 may be 50 μm to 2000 μm, 300 μm to 1200 μm, or 500 μm to 1000 μm.

The microneedles 4 may be needle-shaped convex structures. A shape of each microneedle 4 may be, for example, a polygonal pyramid, such as a quadrangular pyramid, or a cone. Microneedles 4 are a microstructures, and a length (a height) $H_M$ of each microneedle 4 in a direction perpendicular to the main surface of the substrate 2 is preferably 50 μm to 600 μm, 100 μm to 500 μm, or 300 μm to 500 μm, for example.

The microneedles 4 are disposed on the main surface of the substrate in, for example, a square lattice pattern, a rectangular lattice pattern, an orthorhombic lattice pattern, a 45° staggered pattern, or a 60° staggered pattern.

A density (a needle density) at which the microneedles 4 are disposed on the substrate 2 is represented by the number of the microneedles 4 per unit area in a region substantially having the microneedles 4. The region substantially having the microneedles 4 is a region obtained by connecting the outermost microneedles 4 among the plurality of microneedles 4 disposed in the microneedle device 10. From the viewpoint of introducing a larger amount of biologically active substance into the skin, the needle density may be, for example, 10 needles/cm$^2$ or more, 50 needles/cm$^2$ or more, or 100 needles/cm$^2$ or more. From the viewpoint of reducing skin irritation, the needle density may be, for example, 850 needles/cm$^2$ or less, 500 needles/cm$^2$ or less, 200 needles/cm$^2$ or less, or 160 needles/cm$^2$ or less.

Examples of a material of the substrate 2 or the microneedles 4 include silicon, silicon dioxide, ceramics, metals, polysaccharides, and synthetic or natural resin materials. Examples of polysaccharides include pullulan, chitin, and chitosan. The resin material may be, for example, a biodegradable polymer such as polylactic acid, polyglycolide, polylactic acid-co-polyglycolide, polycaprolactone, polyurethane, a polyamino acid (for example, poly-γ-aminobutyric acid) or the like, or may be a non-degradable polymer such as polycarbonate, polymethacrylic acid, ethylene vinyl acetate, polytetrafluoroethylene, polyoxymethylene, or a cyclic olefin copolymer.

In the coating step in the method of manufacturing the microneedle device 10 according to one embodiment of the present invention, the coating liquid is coated on the microneedles 4. The coating liquid comprises a biologically active substance and a sulfated polysaccharide.

The biologically active substance is a substance that exhibits a therapeutic or prophylactic effect in a subject to which it is administered. The biologically active substance may be, for example, peptides, proteins, nucleic acids such as DNA and RNA, sugars, glycoproteins, or other high-molecular or low-molecular compounds.

Specific examples of the biologically active substance include dexmedetomidine, interferon α, interferon β for multiple sclerosis, erythropoietin, follitropin β, follitropin α, G-CSF, GM-CSF, human chorionic gonadotropin, luteinizing hormone, follicle stimulating hormone (FSH), salmon calcitonin, glucagon, GNRH antagonist, insulin, luteinizing hormone releasing hormone (LHRH), human growth hormone, parathyroid hormone (PTH), filgrastin, somatropin, incretin, GLP-1 analogues (for example, exenatide, liraglutide, lixisenatide, albiglutide, and taspoglutide), snake venom peptide analogues, γ globulin, Japanese encephalitis vaccine, hepatitis B vaccine, rotavirus vaccine, Alzheimer's disease vaccine, arteriosclerosis vaccine, a cancer vaccine, nicotine vaccine, diphtheria vaccine, tetanus vaccine, pertussis vaccine, lyme disease vaccine, rabies vaccine, pneumococcal vaccine, yellow fever vaccine, cholera vaccine, vaccinia vaccine, tuberculosis vaccine, rubella vaccine, measles vaccine, influenza vaccine, mumps vaccine, botulinum vaccine, herpes virus vaccine, and pharmaceutically acceptable salts thereof. The biologically active substance may be, for example, dexmedetomidine or dexmedetomidine hydrochloride. The coating liquid may comprise one biologically active substance, or may comprise a plurality of biologically active substances.

In the present invention, the sulfated polysaccharide is a component (a carrier) which assists in carrying the coating liquid on the microneedles 4. The sulfated polysaccharide has an affinity for skin tissues and is excellent in improving absorbability of biologically active substances into the skin. The sulfated polysaccharide is a polysaccharide with a sulfuric acid bound to a hydroxyl group or amino group.

The polysaccharide in the sulfated polysaccharide may be a natural polysaccharide or may be a semi-synthetic or synthetic polysaccharide. A main structure of the polysaccharide is preferably a mucopolysaccharide (also known as glycosaminoglycan). The mucopolysaccharide is a heteropolysaccharide having uronic acid and hexosamine as sugar units. A sulfate moiety in the sulfated polysaccharide may be in the form of a free acid or may form a salt. The sulfate moiety is preferably a monovalent metal salt, particularly a sodium salt. The coating liquid may comprise one sulfated polysaccharide or may comprise a plurality of sulfated polysaccharides.

Examples of a natural or biologically-derived sulfated polysaccharide include chondroitin sulfate, carrageenan, fucoidan, ascophyllan, heparin, heparan sulfate, heparin analogues (heparinoids), keratan sulfate, funoran, porphyran, agaropectin, furcellaran, rhamnan sulfate, glucuronoxylorhamnan sulfate, xyloarabinogalactan sulfate, glucuronoxylorhamnogalactan sulfate, and arabinan sulfate, and salts thereof. Examples of the semi-synthetic or synthetic sulfated polysaccharide include, for example, sulfated dextran, sulfated pentosan, sulfated curdlan, and sulfated cellulose, and salts thereof.

Examples of the sulfated polysaccharide having a mucopolysaccharide as a main structure include chondroitin sulfate, heparin, heparan sulfate, heparinoid, and keratan sulfate, and salts thereof. Among them, chondroitin sulfate and salts thereof are more preferable. A scope of the chondroitin sulfate includes chondroitin sulfate A, chondroitin sulfate B (dermatan sulfate), chondroitin sulfate C, chondroitin sulfate D, chondroitin sulfate E, chondroitin sulfate H, and chondroitin sulfate K.

Examples of the salt of chondroitin sulfate include salts with alkali metals such as sodium and potassium, salts with alkaline earth metals such as calcium and magnesium, salts with other metals such as aluminum, and salts with organic bases. The salt of chondroitin sulfate is preferably an alkali metal salt of chondroitin sulfate, more preferably sodium chondroitin sulfate.

The origin of the chondroitin sulfate and the salts thereof is not limited. The chondroitin sulfate and the salts thereof may be obtained from mammals such as pigs, fish such as salmon and sharks, or microorganisms.

Sulfated polysaccharides tend to have common physical, chemical, and physiological properties due to the presence of sulfate groups. As the proportion of sulfate groups in the sulfated polysaccharide increases, the affinity for water, water retentivity and the thickening effect increase, but the proportion of sulfate groups in the sulfated polysaccharide is not particularly limited. The number of sulfate groups in the sulfated polysaccharide may be 0.25N to 2N, preferably 0.5N to 1.5N per N sugar units mainly constituting the polysaccharide. When the polysaccharide has two main sugar units, the number of sulfate groups may be 0.5 to 4, preferably 1 to 3 per disaccharide unit mainly constituting the polysaccharide.

A viscosity average molecular weight of the sulfated polysaccharide may be, for example, 1000 Da to 500,000 Da, 1000 Da to 100,000 Da or 7000 Da to 40,000 Da, but is not limited thereto. The viscosity average molecular weight may be calculated from a limiting viscosity obtained in accordance with the viscosity measurement Method 1: Viscosity measurement by capillary tube viscometer in General Tests of the Japanese Pharmacopoeia, 15th edition, using the Mark-Houwink-Sakurada equation.

The coating liquid comprises at least one or more solvents that dissolves the biologically active substance and the sulfated polysaccharide. Examples of the solvent include water, polyhydric alcohols, lower alcohols, and triacetin. Water is preferable because it dissolves the sulfated polysaccharide well. Water is also preferable in that it also dissolves dexmedetomidine or pharmaceutically acceptable salts thereof well.

The coating liquid may further comprise other components (for example, a stabilizer, a pH adjuster, a component that promotes entry of the biologically active substance into blood, oils and fats, or inorganic substances) in addition to the biologically active substance, the sulfated polysaccharide, and the solvent. However, it is preferable that the coating liquid does not comprise a surfactant, a monosaccharide, and a disaccharide. Surfactants, monosaccharides, and disaccharides may reduce the surface tension and viscosity of the coating liquid and may reduce the amount of the biologically active substance carried per one microneedle 4.

The stabilizer has, for example, an action in which oxygen oxidation and photooxidation of each component are suppressed and the biologically active substance is stabilized. Examples of the stabilizer are L-cysteine, sodium pyrosulfite, sodium bisulfite, ascorbic acid, ethylenediaminetetraacetic acid (EDTA) or salts thereof, or dibutylhydroxytoluene (BHT). These stabilizers may be used alone or in combination of two or more.

As the pH adjuster, those commonly used in the industry may be used. Examples of the pH adjuster include inorganic acids or organic acids, alkalis, salts, amino acids, or a combination thereof.

A concentration of the sulfated polysaccharide in the coating liquid may be, for example, 0.1 mass % or more, 0.5 mass % or more, 1 mass % or more, 1.3 mass % or more, 1.5 mass % or more, 2 mass % or more, 3 mass % or more, or 4 mass % or more, and may be 20 mass % or less, 16 mass % or less, 15 mass % or less, 14 mass % or less, 13 mass % or less, 12 mass % or less, 11 mass % or less, 10 mass % or less, 9 mass % or less, or 8 mass % or less. From the viewpoint of manufacturing the microneedle device 10 capable of carrying and administering more biologically active substance per one microneedle, the concentration of the sulfated polysaccharide in the coating liquid may be, for example, 1.3 mass % to 11 mass %, 1.5 mass % to 10 mass %, 2 mass % to 10 mass %, 0.5 mass % to 16 mass %, 0.5 mass % to 10 mass %, or 4.0 mass % to 10 mass %.

The concentration of the biologically active substance in the coating liquid may be adjusted according to the type of the biologically active substance, the purpose of treatment, the condition of disease, the condition of the patient, and the nature of the solvent. The concentration of the biologically active substance in the coating liquid may be, for example, 0.01 mass % to 90 mass %, 0.1 mass % to 80 mass %, and 1 mass % to 70 mass %.

A mass ratio of the sulfated polysaccharide to the biologically active substance in the coating liquid may be, for example, 0.01 or more, 0.02 or more, 0.025 or more, 0.03 or more, 0.035 or more, 0.04 or more, 0.05 or more, or 0.08 or more, and also may be 0.36 or less, 0.35 or less, 0.3 or less, 0.27 or less, 0.26 or less, 0.24 or less, 0.23 or less, 0.20 or less, 0.18 or less, or 0.17 or less. When the biologically active substance is dexmedetomidine or a pharmaceutically acceptable salt thereof, the mass ratio is preferably 0.011 to 0.222, 0.044 to 0.222, or 0.089 to 0.222.

The total amount of the other components other than the biologically active substance, the sulfated polysaccharide, and the solvent may be, for example, 80 mass % or less, 60 mass % or less, 30 mass % or less, or 20 mass % or less with respect to the total mass of the coating liquid. The coating liquid may comprise no other components other than the biologically active substance, the sulfated polysaccharide, and the solvent.

The concentration of each component contained in the coating liquid may be measured, for example, by liquid chromatography. Further, the concentration of each component other than the biologically active substance may also be calculated based on the concentration of the biologically active substance measured by a liquid chromatography method and the proportion of each component at the time of formulating the coating liquid.

From the viewpoint of coating the microneedles 4 with a larger amount of coating liquid and the viewpoint of forming the coating 6 on a tip portion of each microneedle 4, a viscosity of the coating liquid at 25° C. is preferably 500 mPa·s to 30,000 mPa·s, more preferably 1000 mPa·s to 10,000 mPa·s. From the same viewpoints, a surface tension of the coating liquid is preferably 10 mN/m to 100 mN/m, more preferably 20 mN/m to 80 mN/m.

The method of coating the microneedles 4 with the coating liquid is not particularly limited, and the coating liquid may be coated by inkjet coating or dip coating, for example. Among these, dip coating is preferred. In the dip coating, the microneedles 4 are coated with the coating liquid by dipping the microneedles 4 in a reservoir in which the coating liquid is stored to a certain depth and then withdrawing the microneedles 4 from the reservoir.

Here, according to the coating liquid of the present invention comprising the sulfated polysaccharide, the microneedles 4 may be coated with a large amount of coating liquid, and thus, it is possible to manufacture the microneedle device 10 in which a larger amount of biologically active substance can be carried and administered per one microneedle.

The amount of the coating liquid coated on the microneedles 4 may be adjusted by the depth to which the microneedles 4 are dipped, for example, in the case of application by dip coating. Here, the depth to which the microneedles 4 are dipped indicates the distance from apexes of the dipped microneedles 4 to a surface of the coating liquid. The dipping depth depends on the length $H_M$ of the microneedle 4, but may be $H_M/2$ or less, for example. Among the biologically active substance contained in the coating 6 formed by drying the coating liquid, the biologically active substance contained in a portion formed in a base portion of the microneedle 4 is less likely to be introduced into the skin compared to the biologically active substance contained in a portion formed in a tip portion of the microneedle 4. Therefore, a larger amount of the coating liquid is preferably coated, mainly, on the tip portion of the microneedle 4. Here, the tip portion of the microneedle 4 is a portion in which a length measured from the apex of the microneedle 4 in a direction perpendicular to the main surface (that is, the base portion) of the substrate 2 is, for example, within 50% of the length $H_M$ of the microneedle 4, as will be described later.

In a drying step after the coating step, the coating liquid may be dried to form the coating 6 on the microneedles 4. Here, drying the coating liquid means volatilizing some or the whole of the solvent contained in the coating liquid. The drying of the coating liquid may be performed by, for example, a method such as air drying, vacuum drying, freeze drying, or a combination thereof. The preferred drying method is air drying.

Here, since the coating liquid according to the present invention comprising the sulfated polysaccharide has high viscosity and surface tension, downward flowing and spreading of the coating liquid before or during the drying of the coating liquid due to gravity can be further reduced. Therefore, even when then the coating liquid is dried with the microneedle array placed in such a way that the microneedles 4 face upward, the coating 6 can be formed mainly on the tip portions of the microneedles 4.

The coating step and the drying step may be performed repeatedly. The amount of the coating 6 formed can be further increased by repeating these steps.

The microneedle device 10 according to one embodiment of the present invention manufactured by the above-described method comprises the coating 6 comprising the biologically active substance and the sulfated polysaccharide on the microneedles 4.

The details of the microneedle array, the biologically active substance, and the sulfated polysaccharide which constitute the microneedle device 10 are as described above. The coating 6 is a coating obtained by removing some or the whole of the solvent from the above-described coating liquid. Therefore, the coating liquid and the coating 6 described above have the same components except for the solvent.

The amount of the sulfated polysaccharide may be, for example, 0.5 parts by mass or more, 1 part by mass or more, 1.9 parts by mass or more, 2 parts by mass or more, 2.5 parts by mass or more, 3 parts by mass or more, 3.5 parts by mass or more, 5.0 parts by mass or more, or 8.0 parts by mass or more, and may also be 27 parts by mass or less, 25 parts by mass or less, 22 parts by mass or less, 21 parts by mass or less, 20 parts by mass or less, 19 parts by mass or less, 18 parts by mass or less, 17 parts by mass or less, 14 parts by mass or less, or 13 parts by mass or less, with respect to 100 parts by mass of the coating 6.

The amount of the biologically active substance may be, for example, 99 parts by mass or less, 95 parts by mass or less, 92 parts by mass or less, 90 parts by mass or less, 89 parts by mass or less, 88 parts by mass or less, or 87.5 parts by mass or less, or 87 parts by mass or less, and may also be 65 parts by mass or more, 70 parts by mass or more, 72 parts by mass or more, 73 parts by mass or more, 74 parts by mass or more, 75 parts by mass or more, 77 parts by mass or more, 78 parts by mass or more, 79 parts by mass or more, or 81 parts by mass or more. with respect to 100 parts by mass of the coating 6.

A mass ratio of the sulfated polysaccharide to the biologically active substance in the coating 6 may be, for example, 0.01 or more, 0.02 or more, 0.025 or more, 0.03 or more, 0.035 or more, 0.04 or more, 0.05 or more, or 0.08 or more, and may also be 0.36 or less, 0.35 or less, 0.3 or less, 0.27 or less, 0.26 or less, 0.24 or less, 0.23 or less, 0.20, 0.18 or less, or 0.17 or less. When the biologically active substance is dexmedetomidine or a pharmaceutically acceptable salt thereof, the mass ratio is preferably, for example, 0.011 to 0.222, 0.044 to 0.222, or 0.089 to 0.222.

The total amount of the other components other than the biologically active substance, the sulfated polysaccharide, and the solvent may be, for example, 95 parts by mass or less, 75 parts by mass or less, 50 parts by mass or less, or 30 parts by mass or less, with respect to 100 parts by mass of the solid content in the coating 6. In the present specification, the solid content refers to the component which remains when the solvent is removed from the coating liquid.

A preferable amount of the biologically active substance carried per one microneedle 4 depends on the type of the biologically active substance, the purpose of treatment, the condition of disease, and the condition of the patient. When the biologically active substance is dexmedetomidine or a pharmaceutically acceptable salt thereof, the amount of dexmedetomidine or the pharmaceutically acceptable salt thereof carried per one microneedle 4 is preferably 390 ng or more, 451 ng or more, or 670 ng or more, from the viewpoint of exhibiting a sufficient drug effect. The upper limit of the amount of the biologically active substance carried per one microneedle 4 is not particularly limited, but may be, for example, 2 μg or less, 1 μg or less, 755 ng or less, 545 ng or less, or 500 ng or less. The amount of the sulfated polysaccharide carried per one microneedle 4 may be, for example, 15 ng to 100 ng, 21 ng to 97 ng, 5 ng to 149 ng, or 67 ng to 149 ng. The amount of the coating 6 carried per one microneedle 4 may be, for example, 490 ng to 700 ng, 516 ng to 642 ng, 456 ng to 836 ng, or 819 ng to 836 ng.

The amount of each component contained in the coating 6 may be measured by, for example, a liquid chromatography method. Further, the amount of each component other than the biologically active substance may also be calculated based on the amount of the biologically active substance measured by the liquid chromatography method and the proportion of each component at the time of formulating the coating liquid. The amount of each component carried per one microneedle 4 may be obtained by dividing a value thus measured or calculated by the number of microneedles.

When there are a plurality of microneedles 4, the coating 6 may be formed on all the microneedles 4 or may be formed on only some of the microneedles 4. The coating 6 may be formed only on the tip portion of the microneedle 4, or may be formed to cover the entire microneedle 4. The coating 6 is preferably formed on the tip portion of the microneedle 4. Here, the tip portion of the microneedle 4 is a portion in which a length measured from the apex of the microneedle 4 in a direction perpendicular to the main surface (that is, the base portion) of the substrate 2 is, for example, within 50%, within 40%, within 30%, or within 20% of the length $H_M$ of the microneedle 4. An average thickness of the coating 6 may be less than 50 μm and may be 1 μm to 30 μm.

EXAMPLES

<Test Example 1> Comparison of Carriers

Coating liquids 1 to 4 were prepared by mixing components shown in Tables 1 and 2. In Table, γ-PGA is γ-polyglutamic acid. A pharmaceutical grade product of Maruha Nichiro Corporation was used as sodium chondroitin sulfate (hereinafter, may be referred to as CSNa). As the pullulan, a pharmaceutical product of Hayashibara Co., Ltd. was used. A product of Nippon Poly-Glu Co., Ltd. was used as γ-PGA. "Kuraray Poval PVA-205" (degree of saponification: about 87.0 mol % to 89.0 mol %, degree of polymerization: about 500) manufactured by Kuraray Co., Ltd. was used as polyvinyl alcohol.

TABLE 1

| Component | | Concentration (mass %) |
| --- | --- | --- |
| Biologically active substance | Dexmedetomidine hydrochloride | 45 |
| Carrier | Refer to Table 2 | 8 |
| Stabilizer | L-cysteine | 5 |
| Water for injection | | 42 |
| Sum | | 100 |

TABLE 2

| Coating liquid | Carrier |
| --- | --- |
| 1 (Example) | Sodium chondroitin sulfate |
| 2 (Comparative example) | Pullulan |
| 3 (Comparative example) | γ-PGA |
| 4 (Comparative example) | Polyvinyl alcohol |

For the coating liquids 1 and 2, a contact angle with the microneedles of polylactic acid, a surface tension, and a viscosity were measured. The contact angle was measured by a droplet method (a θ/2 method) (temperature of 23° C. to 25° C.). The surface tension was calculated by a pendant drop method using an empirical equation of Andreas et al. (temperature of 24° C.). The viscosity was obtained from a pressure loss in a capillary channel (temperature of 23° C. to 25° C.). The results are shown in Table 3.

TABLE 3

| Coating liquid | Carrier | Contact angle | Surface tension (mN/m) | Viscosity (mPa · s) |
| --- | --- | --- | --- | --- |
| 1 | Sodium chondroitin sulfate | 103.9° | 42.5 | 3151 |
| 2 | Pullulan | 96.4° | 41.9 | 3243 |

As shown in Table 3, the surface tension and the viscosity were not significantly different between the coating liquid containing sodium chondroitin sulfate and the coating liquid containing pullulan.

Next, a microneedle array of polylactic acid in which microneedles were provided at a density of 156/cm$^2$ in a region of 1 cm$^2$ and the shape of each microneedle was a quadrangular pyramid having a height of 500 μm was prepared, and then the microneedles were dipped in the coating liquids 1 to 4 to a depth of about 140 μm. After the microneedles were pulled up from the coating liquids, the solvents of the coating liquids 1 to 4 on the microneedles were dried to obtain microneedle devices 1 to 4.

Figure 2:
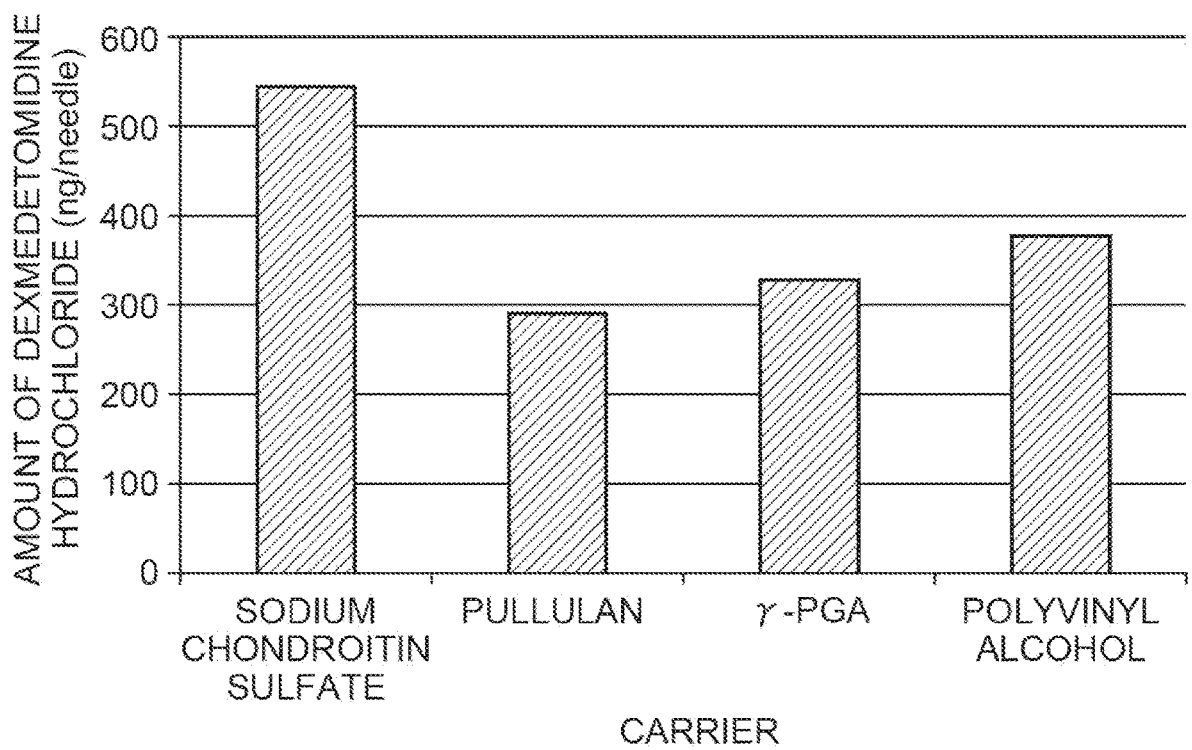
FIG. 2 is a graph showing a relationship between the type of carrier and the amount of dexmedetomidine hydrochloride carried per one microneedle.

After the solvents were dried, the amount of dexmedetomidine hydrochloride in the coating formed on the microneedles was quantified by a high performance liquid chromatography method, and the amount of the carrier and the amount of the coating per one microneedle were calculated therefrom. The results are shown in Table 4 and FIG. 2.

TABLE 4

| Microneedle device | Carrier | Dexmedetomidine hydrochloride (ng/needle) | Carrier (ng/needle) | Coating (ng/needle) |
| --- | --- | --- | --- | --- |
| 1 (Example) | Sodium chondroitin sulfate | 545 | 97 | 702 |
| 2 (Comparative example) | Pullulan | 290 | 52 | 374 |
| 3 (Comparative example) | γ-PGA | 327 | 58 | 421 |
| 4 (Comparative example) | Polyvinyl alcohol | 377 | 67 | 486 |

By using sodium chondroitin sulfate as the carrier, it was possible to manufacture a microneedle device carrying a larger amount of biologically active substance per one microneedle compared to the case of using pullulan (nonionic polysaccharide), polyvinyl alcohol (nonionic polymer), and γ-PGA.

<Test Example 2> Comparison of Composition of Coating Liquids

Dexmedetomidine hydrochloride, sodium chondroitin sulfate, L-cysteine (stabilizer) and water for injection were mixed to prepare coating liquids 5 to 13 (Examples) shown in Table 5. The details of the sodium chondroitin sulfate used are the same as in Test Example 1. A microneedle array of polylactic acid in which microneedles were provided at a density of 156/cm² in a region of 1 cm² and the shape of each microneedle was a quadrangular pyramid having a height of 500 μm was prepared, and then the microneedles were dipped in the coating liquids 5 to 13 to a depth of about 140 μm. After the microneedles were pulled up from the coating liquids, the solvents of the coating liquids 5 to 13 on the microneedles were dried to obtain microneedle devices 5 to 13 (Examples).

TABLE 5

| Coating liquid | Dexmedetomidine hydrochloride (mass %) | Sodium chondroitin sulfate (mass %) | L-cysteine (mass %) | Water (mass %) | Mass ratio of sodium chondroitin sulfate/dexmedetomidine hydrochloride |
|---|---|---|---|---|---|
| 5 | 45 | 0.5 | 5 | 49.5 | 0.011 |
| 6 | 45 | 1 | 5 | 49 | 0.022 |
| 7 | 45 | 2 | 5 | 48 | 0.044 |
| 8 | 45 | 4 | 5 | 46 | 0.089 |
| 9 | 45 | 6 | 5 | 44 | 0.133 |
| 10 | 45 | 8 | 5 | 42 | 0.178 |
| 11 | 45 | 10 | 5 | 40 | 0.222 |
| 12 | 45 | 12 | 5 | 38 | 0.267 |
| 13 | 45 | 14 | 5 | 36 | 0.311 |

After the solvents were dried, the amount of dexmedetomidine hydrochloride in the coating formed on the microneedles was quantified by a high performance liquid chromatography method, and the amount of the carrier and the amount of the coating per one microneedle were calculated therefrom. The results are shown in Table 6.

TABLE 6

| Microneedle device | Amount of dexmedetomidine hydrochloride (ng/needle) | Amount of sodium chondroitin sulfate (ng/needle) | Amount of coating (ng/needle) |
|---|---|---|---|
| 5 | 335 | 4 | 376 |
| 6 | 358 | 8 | 406 |
| 7 | 486 | 22 | 562 |
| 8 | 449 | 40 | 539 |
| 9 | 458 | 61 | 570 |
| 10 | 400 | 71 | 516 |
| 11 | 437 | 97 | 583 |
| 12 | 321 | 86 | 442 |
| 13 | 265 | 82 | 377 |

Figure 3:
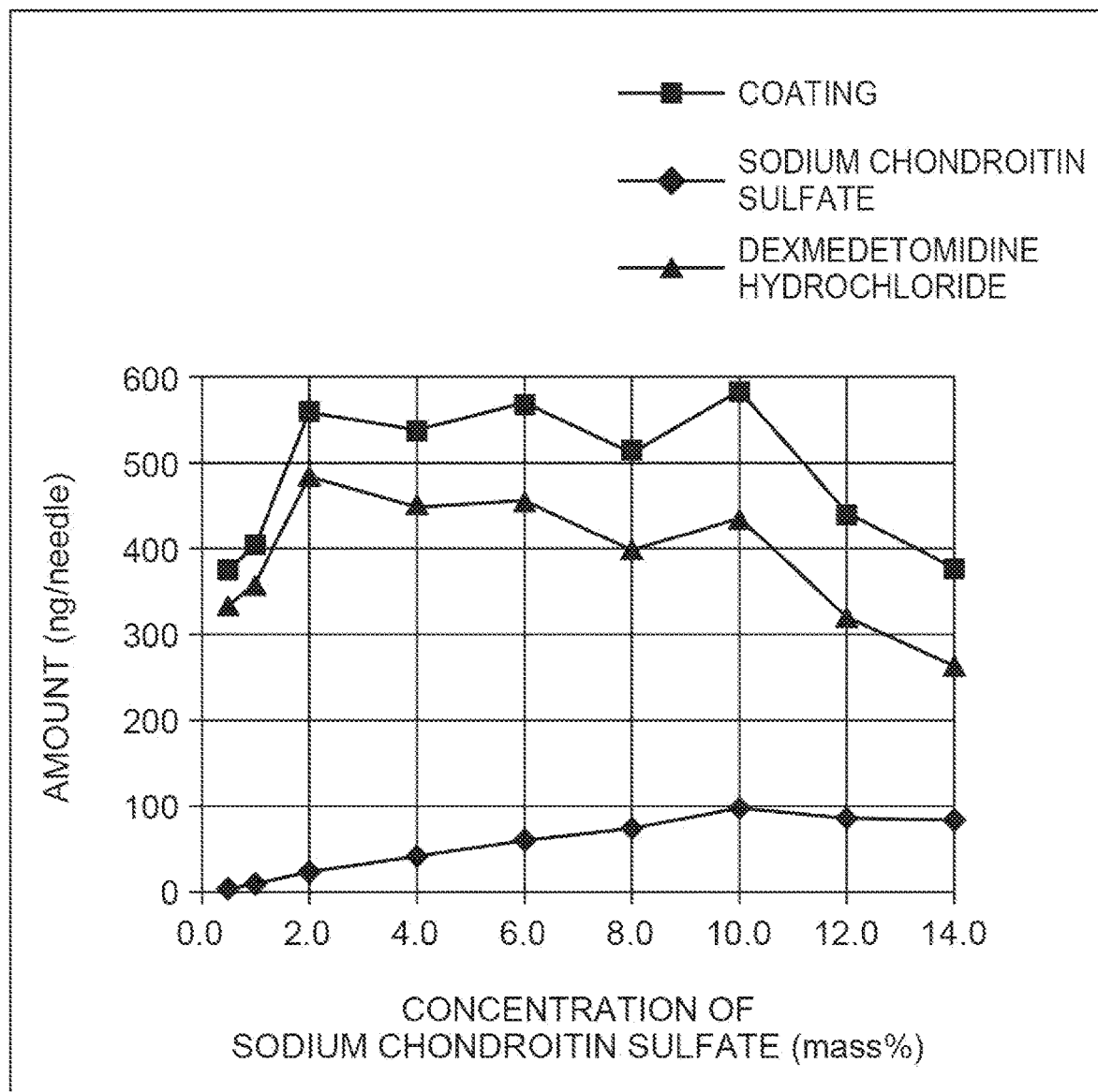
FIG. 3 is a graph in which the amount of coating per one microneedle and the amounts of dexmedetomidine hydrochloride and sodium chondroitin sulfate contained therein are plotted with respect to the concentration (mass %) of sodium chondroitin sulfate in the coating liquid.

FIG. 3 is a graph in which the amount of coating per one microneedle and the amounts of dexmedetomidine hydrochloride and carriers contained therein are plotted with respect to the concentration (mass %) of sodium chondroitin sulfate in the coating liquid. As shown in FIG. 3, it was possible to manufacture a microneedle device carrying even larger amount of dexmedetomidine hydrochloride per one microneedle by adding sodium chondroitin sulfate in the coating liquid at a concentration in a specific range.

Figure 4:
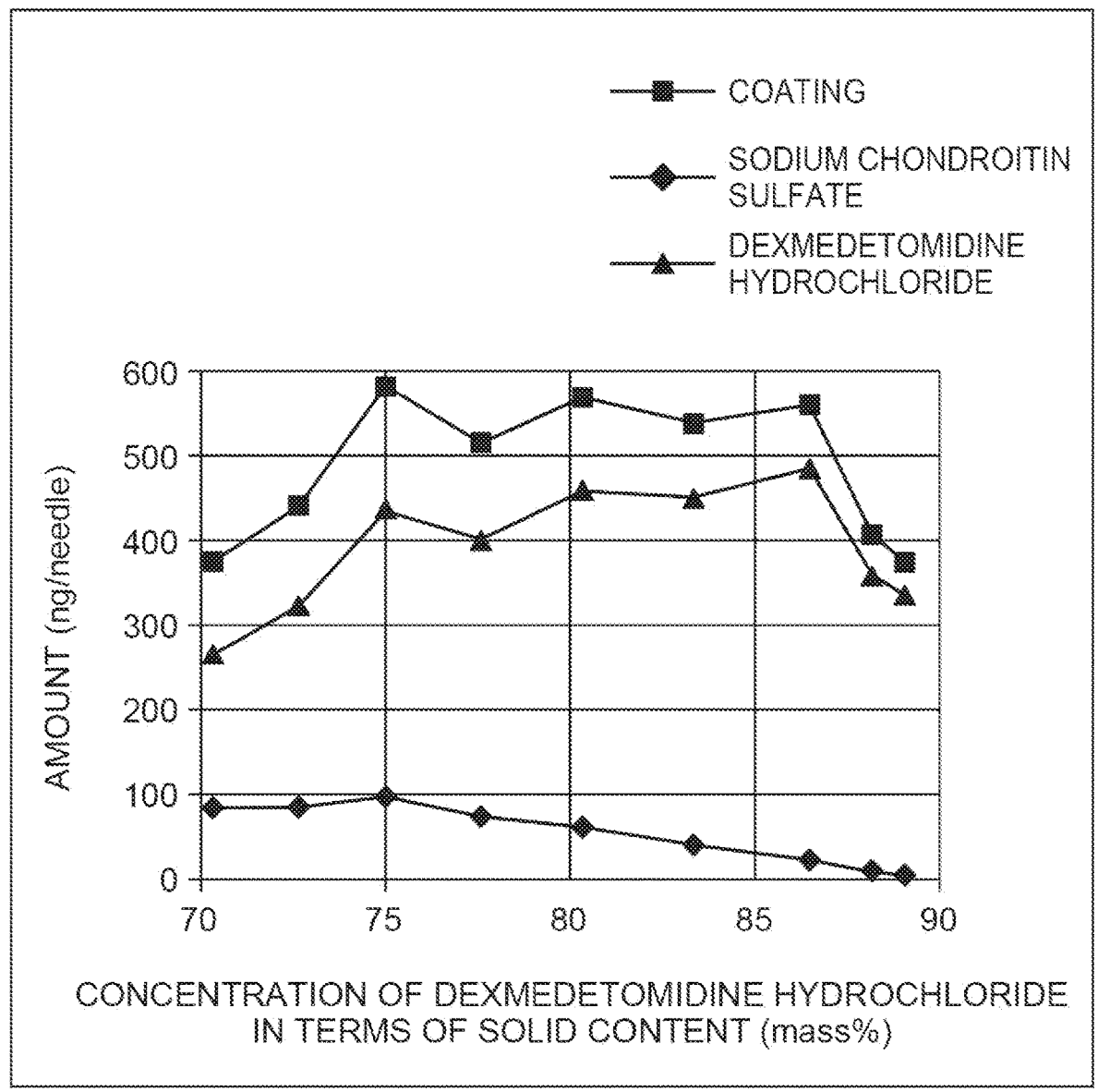
FIG. 4 is a graph in which the amount of coating per one microneedle and the amounts of dexmedetomidine hydrochloride and sodium chondroitin sulfate contained therein are plotted with respect to a concentration (mass %) of dexmedetomidine hydrochloride in the coating liquid in terms of a solid content.

FIG. 4 is a graph in which the horizontal axis of FIG. 3 is changed to the concentration (mass %) of dexmedetomidine hydrochloride in the coating liquid in terms of a solid content. The concentration of dexmedetomidine hydrochloride in terms of a solid content refers to the proportion of dexmedetomidine hydrochloride to the total amount of solid content (dexmedetomidine hydrochloride, sodium chondroitin sulfate, and L-cysteine) in the coating liquid.

Figure 5:
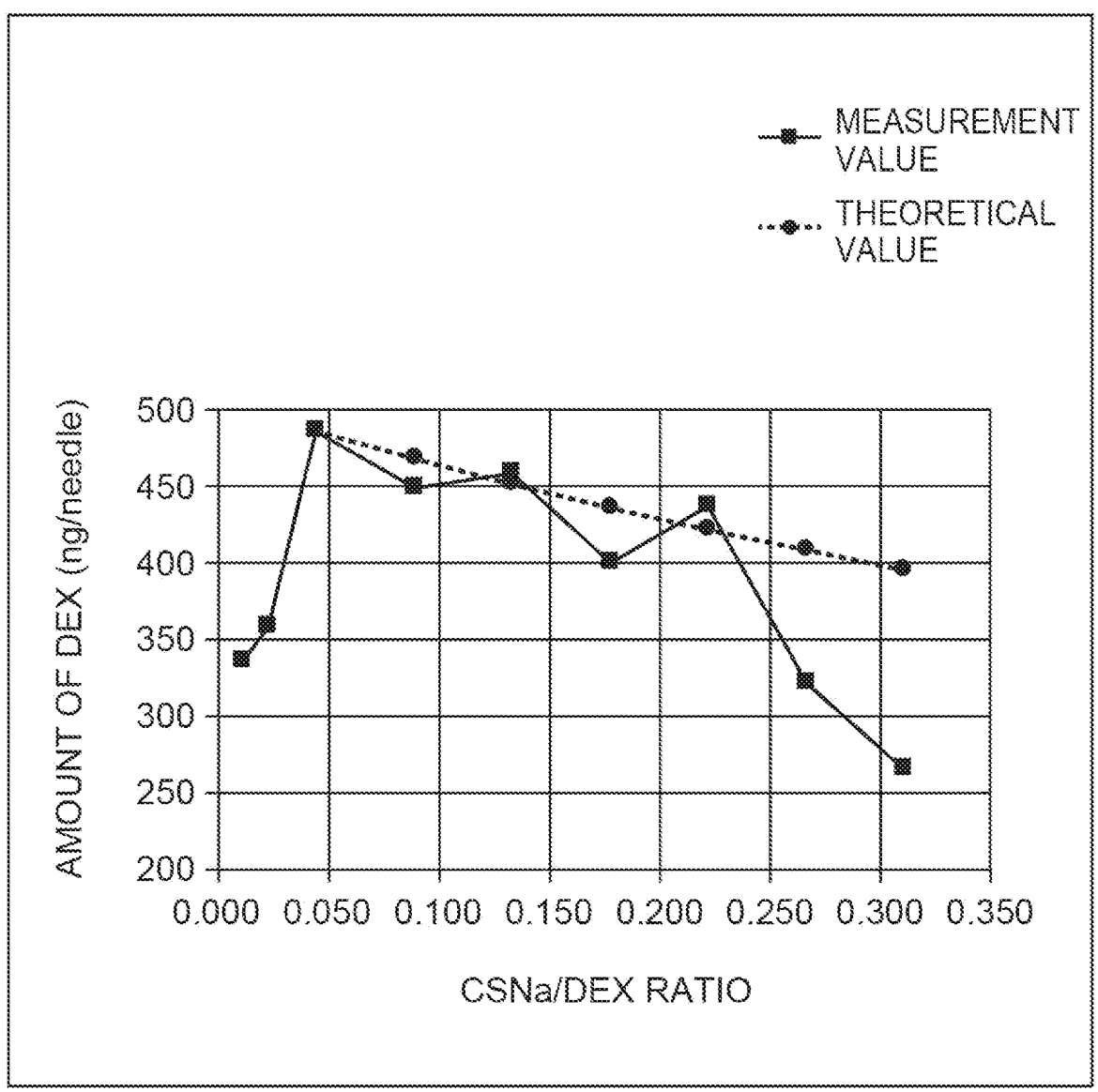
FIG. 5 is a graph in which the amount of dexmedetomidine hydrochloride (amount of DEX) carried per one microneedle is plotted with respect to the mass ratio (CSNa/DEX ratio) of sodium chondroitin sulfate to dexmedetomidine hydrochloride.

FIG. 5 is a graph in which the amount of dexmedetomidine hydrochloride (amount of DEX) carried per one microneedle is plotted, with the mass ratio of sodium chondroitin sulfate to dexmedetomidine hydrochloride (CSNa/DEX ratio) being the horizontal axis. In FIG. 5, a solid line shows a measurement value, and a broken line shows a theoretical value. The theoretical value indicates the amount of DEX estimated to be contained in the coating when the maximum amount of coating was carried per one microneedle. The theoretical value was calculated assuming that the amount of coating (562 ng) carried per one microneedle when the maximum value of the amount of dexmedetomidine hydrochloride in Table 6 (486 ng/needle) was obtained was the maximum amount of coating that can be carried per one microneedle. Equation used for calculating the theoretical value is as follows.

Theoretical value of the amount of DEX (ng/needle)= 562 (ng/needle)×concentration (mass %) of dexmedetomidine hydrochloride in the coating liquid in terms of solid content/100

As shown in FIG. 5, when the CSNa/DEX ratio was 0.044 to 0.222, the measurement value and the theoretical value were substantially the same, although there was some variation. On the other hand, when the CSNa/DEX ratio exceeded 0.222, the measurement value was below the theoretical value, and a difference between the values increased as the CSNa/DEX ratio increased. From these results, it is estimated that, when the CSNa/DEX ratio exceeds 0.222, some kind of change occurs in physical properties of the coating liquid, and this change acts in a way to inhibit the increase in the amount of DEX carried on the microneedles.

<Test Example 3> Comparison of Composition of Coating Liquids

Dexmedetomidine hydrochloride (the biologically active substance), sodium chondroitin sulfate (the carrier), and water for injection were mixed to prepare coating liquids 14 to 23 (Examples) shown in Table 7. The details of the sodium chondroitin sulfate used are the same as in Test example 1. A microneedle array of polylactic acid in which microneedles were provided at a density of 156/cm² in a region of 1 cm² and the shape of each microneedle was a quadrangular pyramid having a height of 500 μm was prepared, and then the microneedles were dipped in the coating liquids 14 to 23 to a depth of about 140 μm. After the microneedles were pulled up from the coating liquids, the solvents of the coating liquids 14 to 23 on the microneedles were dried to obtain microneedle devices 14 to 23.

TABLE 7

| Coating liquid | Dexmedetomidine hydrochloride (mass %) | Sodium chondroitin sulfate (mass %) | Water (mass %) | Mass ratio of sodium chondroitin sulfate/dexmedetomidine hydrochloride | Transparency |
|---|---|---|---|---|---|
| 14 | 45 | 0.5 | 54.5 | 0.011 | Transparent |
| 15 | 45 | 1 | 54 | 0.022 | Transparent |

TABLE 7-continued

| Coating liquid | Dexmedetomidine hydrochloride (mass %) | Sodium chondroitin sulfate (mass %) | Water (mass %) | Mass ratio of sodium chondroitin sulfate/dexmedetomidine hydrochloride | Transparency |
|---|---|---|---|---|---|
| 16 | 45 | 2 | 53 | 0.044 | Transparent |
| 17 | 45 | 4 | 51 | 0.089 | Transparent |
| 18 | 45 | 6 | 49 | 0.133 | Transparent |
| 19 | 45 | 8 | 47 | 0.178 | Transparent |
| 20 | 45 | 10 | 45 | 0.222 | Transparent |
| 21 | 45 | 12 | 43 | 0.267 | Transparent |
| 22 | 45 | 14 | 41 | 0.311 | Transparent |
| 23 | 45 | 16 | 39 | 0.356 | Slightly cloudy |

After the solvents were dried, the amount of dexmedetomidine hydrochloride in the coating formed on the microneedles was quantified by a high performance liquid chromatography method, and the amount of the carrier and the amount of the coating per one microneedle were calculated therefrom. The results are shown in Table 8.

TABLE 8

| Microneedle device | Amount of dexmedetomidine hydrochloride (ng/needle) | Amount of sodium chondroitin sulfate (ng/needle) | Amount of coating (ng/needle) |
|---|---|---|---|
| 14 | 451 | 5 | 456 |
| 15 | 525 | 12 | 537 |
| 16 | 621 | 28 | 648 |
| 17 | 755 | 67 | 822 |
| 18 | 738 | 98 | 837 |
| 19 | 706 | 126 | 831 |
| 20 | 670 | 149 | 819 |
| 21 | 626 | 167 | 793 |
| 22 | 561 | 175 | 736 |
| 23 | 510 | 181 | 691 |

Figure 6:
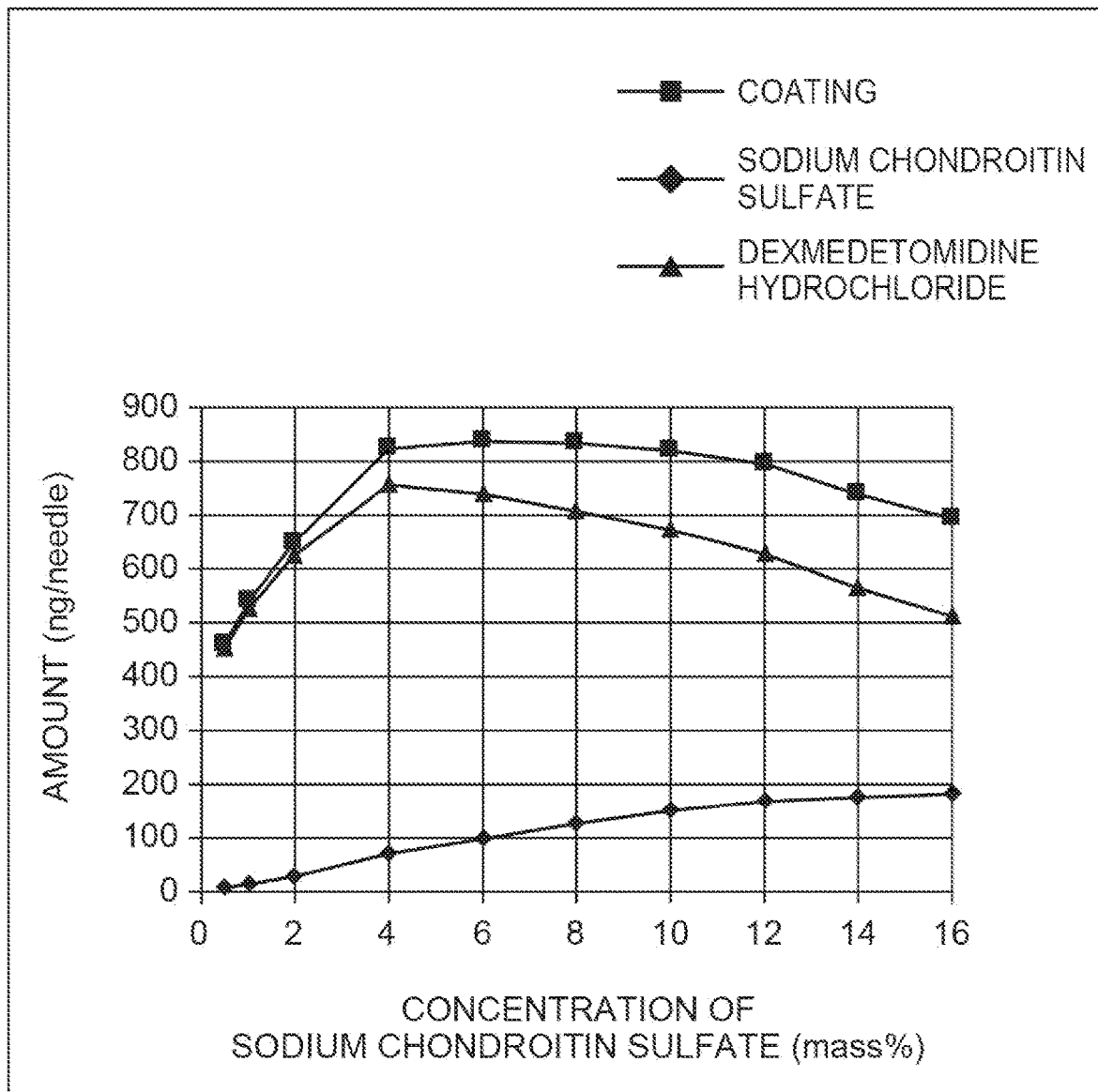
FIG. 6 is a graph in which the amount of coating per one microneedle and the amounts of dexmedetomidine hydrochloride and sodium chondroitin sulfate contained therein are plotted with respect to the concentration (mass %) of sodium chondroitin sulfate in the coating liquid.

FIG. 6 is a graph in which the amount of coating per one microneedle and the amounts of dexmedetomidine hydrochloride and carriers contained therein are plotted with respect to the concentration (mass %) of sodium chondroitin sulfate in the coating liquid. As shown in FIG. 6, it was possible to manufacture a microneedle device carrying even larger amount of dexmedetomidine hydrochloride per one microneedle by adding sodium chondroitin sulfate in the coating liquid at a concentration in a specific range.

Figure 7:
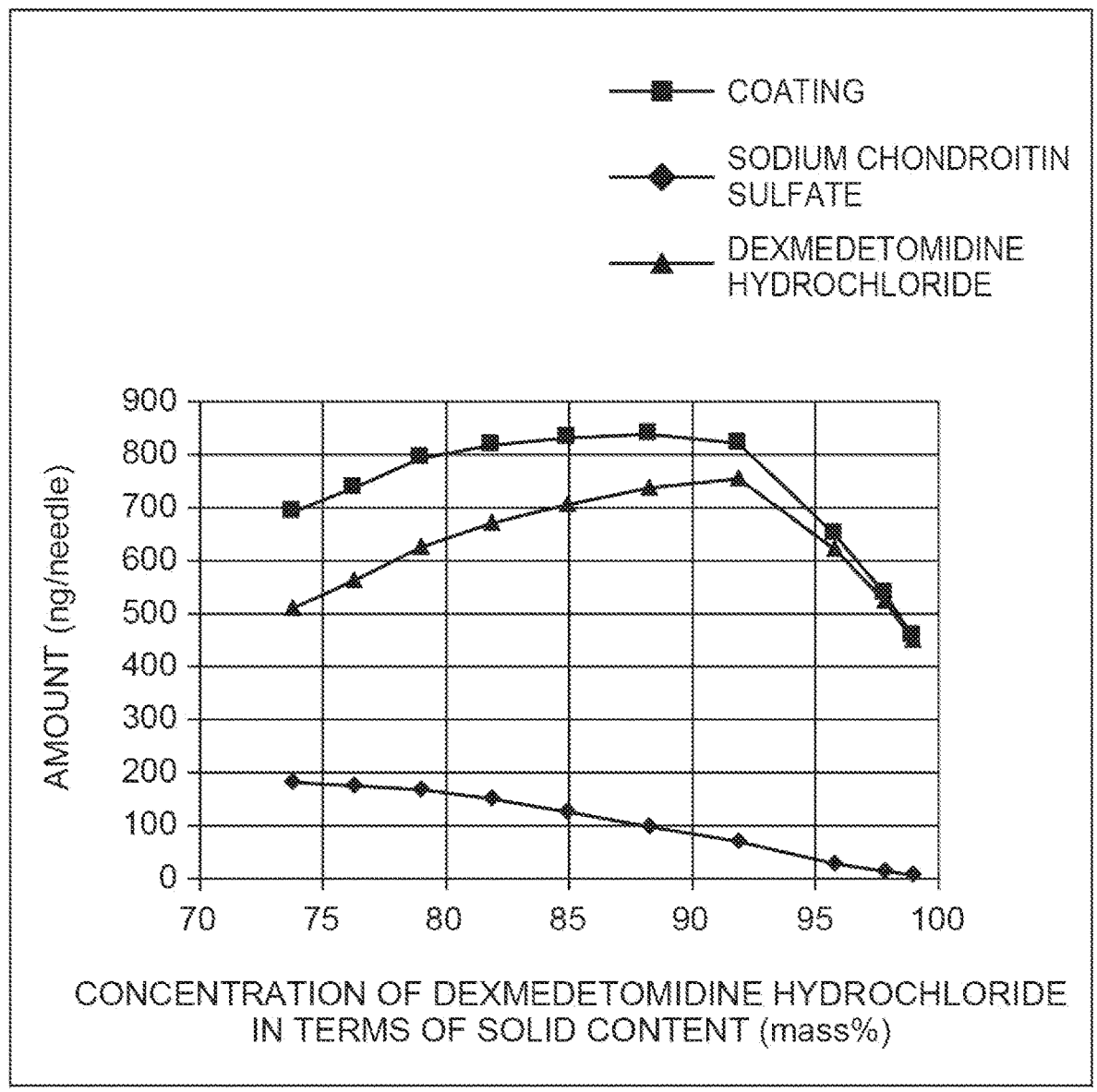
FIG. 7 is a graph in which the amount of coating per one microneedle and the amounts of dexmedetomidine hydrochloride and sodium chondroitin sulfate contained therein are plotted with respect to the concentration (mass %) of dexmedetomidine hydrochloride in the coating liquid in terms of a solid content.

FIG. 7 is a graph in which a horizontal axis of FIG. 6 is changed to the concentration (mass %) of dexmedetomidine hydrochloride in the coating solution in terms of a solid content. The concentration of dexmedetomidine hydrochloride in terms of a solid content refers to the proportion of dexmedetomidine hydrochloride to the total amount of solid content (dexmedetomidine hydrochloride and sodium chondroitin sulfate) in the coating liquid.

Figure 8:
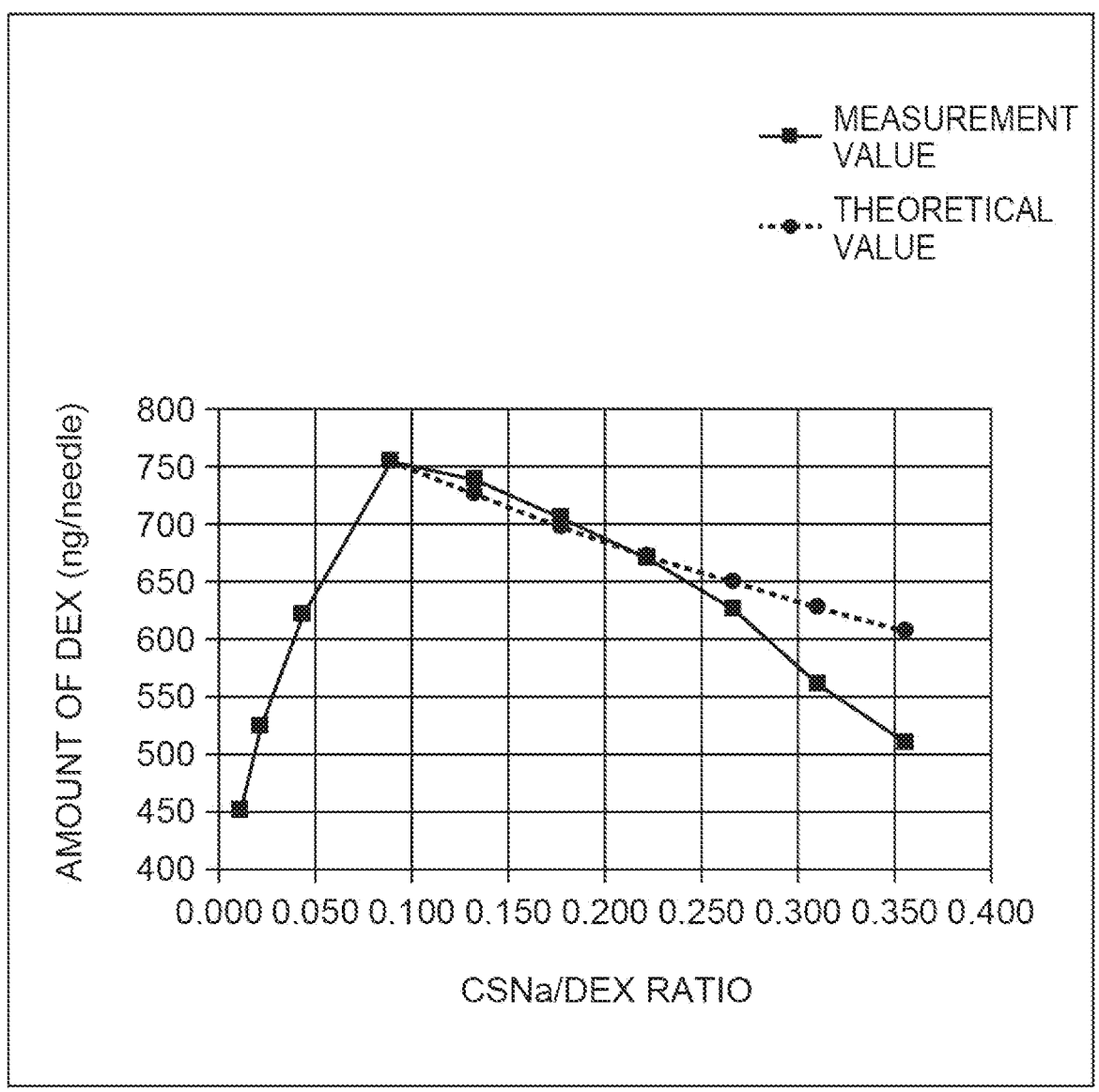
FIG. 8 is a graph in which the amount of dexmedetomidine hydrochloride (amount of DEX) carried per one microneedle is plotted with respect to the mass ratio (CSNa/DEX ratio) of sodium chondroitin sulfate to dexmedetomidine hydrochloride.

FIG. 8 is a graph in which the amount of dexmedetomidine hydrochloride (amount of DEX) carried per one microneedle is plotted, with the mass ratio of sodium chondroitin sulfate to dexmedetomidine hydrochloride (CSNa/DEX ratio) being the horizontal axis. In FIG. 8, a solid line shows a measurement value, and a broken line shows a theoretical value. The theoretical value indicates the amount of DEX estimated to be contained in the coating when the maximum amount of coating was carried per one microneedle. The theoretical value was calculated assuming that the amount of coating (822 ng) carried per one microneedle when the maximum value of the amount of dexmedetomidine hydrochloride in Table 8 (755 ng/needle) was obtained was the maximum amount of coating that can be carried per one microneedle. Equation used for calculating the theoretical value is as follows.

Theoretical value of the amount of DEX (ng/needle)= 822 (ng/needle)×concentration (mass %) of dexmedetomidine hydrochloride in the coating liquid in terms of solid content/100

As shown in FIG. 8, when the CSNa/DEX ratio was 0.089 to 0.222, the measurement value and the theoretical value were substantially the same. On the other hand, when the CSNa/DEX ratio exceeded 0.222, the measurement value was below the theoretical value, and a difference between the values increased as the CSNa/DEX ratio increased. From these results, it is estimated that, when the CSNa/DEX ratio exceeds 0.222, some kind of change occurs in physical properties of the coating liquid, and this change acts in a way to inhibit the increase in the amount of DEX carried on the microneedles.

REFERENCE SIGNS LIST

2 Substrate
4 Microneedle
6 Coating
10 Microneedle device

The invention claimed is:

1. A microneedle device comprising:
a substrate;
microneedles disposed on the substrate; and
a coating formed on the microneedles,
   wherein the coating comprises a biologically active substance and a sulfated polysaccharide;
   wherein a mass ratio of the sulfated polysaccharide to the biologically active substance is 0.044 to 0.222;
   wherein the biologically active substance is dexmedetomidine or a pharmaceutically acceptable salt thereof; and
   wherein the sulfated polysaccharide is sodium chondroitin sulfate.

2. The microneedle device according to claim 1, wherein an amount of the sulfated polysaccharide is 0.5 parts by mass or more with respect to 100 parts by mass of the coating.

3. The microneedle device according to claim 1, wherein the mass ratio of the sulfated polysaccharide to the biologically active substance is 0.089 to 0.222.

4. The microneedle device according claim 1, wherein the microneedles are disposed on the substrate at a microneedle density of 10 microneedles/cm$^2$ or more and 850 microneedles/cm$^2$ or less.

5. The microneedle device according claim 1, wherein an amount of the biologically active substance carried per one microneedle is 390 ng or more.

6. A method of manufacturing a microneedle device which comprises a substrate, microneedles disposed on the substrate, and a coating formed on the microneedles, the method comprising:
coating the microneedles with a coating liquid,
   wherein the coating liquid comprises a biologically active substance and a sulfated polysaccharide;
   wherein a mass ratio of the sulfated polysaccharide to the biologically active substance is 0.044 to 0.222;

wherein the biologically active substance is dexmedetomidine or a pharmaceutically acceptable salt thereof; and wherein the sulfated polysaccharide is sodium chondroitin sulfate.

7. The method according to claim 6, wherein a concentration of the sulfated polysaccharide in the coating liquid is 0.1 mass percent or more.

8. The method according to claim 6, wherein the mass ratio of the sulfated polysaccharide to the biologically active substance in the coating liquid is 0.089 to 0.222.

* * * * *